United States Patent [19]

Sehring

[11] Patent Number: 4,670,610

[45] Date of Patent: Jun. 2, 1987

[54] PREPARATION OF 2,5-DICHLOROPHENOL

[75] Inventor: Richard H. Sehring, Ingelheim, Fed. Rep. of Germany

[73] Assignee: Sandoz, Inc., Basel, Switzerland

[21] Appl. No.: 710,085

[22] Filed: Mar. 11, 1985

[30] Foreign Application Priority Data

Mar. 10, 1984 [DE] Fed. Rep. of Germany ....... 3408806

[51] Int. Cl.$^4$ ............................................. C07C 39/30
[52] U.S. Cl. .................................... 568/774; 568/776; 568/778
[58] Field of Search ...................... 568/778, 774, 776

[56] References Cited

U.S. PATENT DOCUMENTS

| 2,196,985 | 2/1939 | Flett | 568/774 |
| 2,249,757 | 2/1941 | Flett | 568/774 |
| 2,835,707 | 5/1958 | Stoesser et al. | 568/778 |
| 3,965,158 | 6/1976 | Soula et al. | 568/774 |

FOREIGN PATENT DOCUMENTS 2362648  7/1974  Fed. Rep. of Germany ...... 568/778

OTHER PUBLICATIONS

Galat "J. Amer. Chem. Soc." vol. 74, pp. 3890-3891 (1958).

*Primary Examiner*—Werren B. Lone
*Attorney, Agent, or Firm*—Burns, Doane, Swecker & Mathis

[57] ABSTRACT

2,5-Dichlorophenol is readily and facilely prepared from 2,5-dichloro-4-hydroxybenzenesulfonic acid or salt thereof, said sulfonic acid/sulfonate itself being characteristically produced by hydrolysis of a precursor trichlorobenzenesulfonic acid, by cleaving the sulfo/sulfonate moiety therefrom by treatment, e.g., under reflux, with a constant boiling point hydrobromic acid.

14 Claims, No Drawings

PREPARATION OF 2,5-DICHLOROPHENOL

BACKGROUND OF THE INVENTION

1. Field of the Invention:

The present invention relates to the preparation of 2,5-dichlorophenol, and, more especially, to the preparation of 2,5-dichlorophenol from 1,2,4-trichlorobenzene.

2. Description of the Prior Art:

2,5-Dichlorophenol is a known valuable compound, particularly useful as an intermediate in the production of a wide variety of crop chemicals for, e.g., crop and plant protection.

SUMMARY OF THE INVENTION

It has now surprisingly been found, and which is a major object of the present invention, that a high purity (e.g., but little byproduct), high quality 2,5-dichlorophenol is readily and facilely prepared by (i) first sulfonating 1,2,4-trichlorobenzene into 2,4,5-trichlorobenzenesulfonic acid, (ii) next hydrolyzing said 2,4,5-trichlorobenzenesulfonic acid by known technique to give 2,5-dichloro-4-hydroxybenzenesulfonic acid or salt thereof, and then (iii) removing the sulfo or sulfonate moiety therefrom by treatment with constant boiling hydrobromic acid, advantageously under reflux.

DETAILED DESCRIPTION OF THE INVENTION

More particularly according to the present invention, it has now surprisingly been found that removal of the sulfo group is most readily and effectively carried out by treating the precursor sulfonic acid with an excess of constant boiling point hydrobromic acid (about 48 percent strength). Heretofore, the sulfonic acid function, or sulfo group, was typically cleaved under extreme conditions of high temperature, mandating reaction in an autoclave, the inner wall members of which were easily damaged (by sulfuric acid, phosphoric acid), or which otherwise did not produce a satisfactory result (hydrochloric acid). But by the use of constant boiling point hydrobromic acid consistent herewith, it is unexpectedly found that the sulfo group cleavage reaction need not be carried out in an autoclave, but only under reflux at a base temperature of about 140° C. (reflux temperature 126° C.). The hydrobromic acid employed, moreover, can easily be recovered, and reused or recycled.

In order to further illustrate the present invention and the advantages thereof, the following specific example is given, it being understood that same is intended only as illustrative and in nowise limitative.

EXAMPLE (1) Preparation of 2,4,5-trichlorobenzenesulfonic acid 119 g (1.0 mol) of technical grade chlorosulfonic acid were added dropwise, under stirring, to 218 g (1.2 mol) of technical grade 90% strength 1,2,4-trichlorobenzene over a period of time of about one hour. The reaction was permitted to proceed at 150° to 160° C. for three hours. During the reaction a slow stream of dried air or dried carbon dioxide was passed through the reaction mixture. The resulting hydrogen chloride of reaction was transferred with the gas stream into a receiving flask containing water. The hydrochloric acid trapped in the receiving flask constituted about 96% of theoretical. The reaction mixture, after being cooled to 120° C., was mixed with 200 ml of water. Steam was then charged therein to remove excess trichlorobenzene. 37 g (0.2 mol) of trichlorobenzene were recovered. Water was added to the reaction mixture to provide a total volume of 700 g which was then titrated with sodium hydroxide solution.

Total acid: 1.068 mol,

Sulfuric acid: 0.066 mol (determined as barium sulfate)

The total yield consequently was 1.00 mol of 2,4,5-trichlorobenzenesulfonic acid (262 g).

(2) Preparation of the sodium salt of 2,5-dichloro-4-hydroxybenzenesulfonic acid An iron autoclave was charged with 590 g of water, 273 g of 48% strength aqueous sodium hydroxide solution (3.3 mol) and 700 g of the 37.4% strength aqueous trichlorobenzenesulfonic acid solution obtained in (1). The mixture was heated at 180° C. for 5 hours, the pressure being 7-8 bar.

Upon completion of the reaction, the disodium salt of 2,5-dichloro-4-hydroxybenzenesulfonic acid was present, which, upon addition of dilute sulfuric acid, liberated sodium 2,5-dichloro-4-hydroxybenzenesulfonate.

The yield was about 98% of the theoretical.

(3) Preparation of the 2,5-dichlorophenol 139 g (0.5 mol) of sodium 2,5-dichloro-4-hydroxybenzenesulfonate were added to 400 ml of approximately 48% strength aqueous hydrobromic acid. The mixture was stirred under reflux for 4 hours, during which the base temperature was about 140° C. and the reflux temperature about 126° C. The solution which was still warm, about 60° C., was then stirred with 300 ml of toluene. The toluene phase was separated off, dried and evaporated to dryness. The residue consisted of 70 g of crude 2,5-dichlorophenol (86% of theoretical).

Analysis: calculated Cl, 43.5% found Cl, 43.2%

As the solution containing hydrogen bromide cooled, a slight amount of sodium bromide precipitated. The hydrogen bromide solution could be reused.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of 2,5-dichlorophenol, comprising treating 2,5-dichloro-4-hydroxybenzenesulfonic acid, or salt thereof, with constant boiling point hydrobromic acid.

2. The process as defined by claim 1, comprising treating a salt of 2,5-dichloro-4-hydroxybenzenesulfonic acid with constant boiling point hydrobromic acid.

3. The process as defined by claim 2, comprising refluxing sodium 2,5-dichloro-4-hydroxybenzenesulfonate with a stoichiometric excess of constant boiling point hydrobromic acid.

4. The process as defined by claim 3, comprising refluxing sodium 2,5-dichloro-4-hydroxybenzenesulfonate with a stoichiometric excess of a constant boiling point aqueous solution of hydrobromic acid.

5. A unit process for the preparation of 2,5-dichlorophenol, comprising (i) sulfonating 1,2,4-trichlorobenzene into 2,4,5-trichlorobenzenesulfonic acid, (ii) hydrolyzing/salifying said 2,4,5-trichlorobenzenesulfonic acid into a 2,5-dichloro-4-hydroxybenzenesulfonate, and (iii) converting said sulfonate into 2,5-dichlorophenol by treating same with: constant boiling point hydrobromic acid.

6. The process as defined by claim 5, comprising (iii) converting the sodium sulfonate into 2,5-dichlorophenol by treating same, under reflux, with a stoichiometric excess of a constant boiling point aqueous solution of hydrobromic acid.

7. The process as defined by claim 5, the step (ii) comprising hydrolyzing said 2,4,5-trichlorobenzenesulfonic acid into the disodium salt thereof, and thence converting said disodium salt into sodium 2,5-dichloro-4-hydroxybenzenesulfonate.

8. The process as defined by claim 7, comprising converting said disodium salt by addition of dilute sulfuric acid thereto.

9. A process for the preparation of 2,5-dichlorophenol, comprising treating 2,5-dichloro-4-hydroxybenzenesulfonic acid, or salt thereof, with constant boiling point hydrobromic acid under reflux.

10. The process as defined by claim 9 wherein said treating comprises a base temperature of about 140° C. and a reflux temperature of about 126° C.

11. The process as defined by claim 10 wherein said treating occurs at substantially atmospheric pressure.

12. The process as defined by claim 5 wherein said treating occurs under reflux.

13. The process as defined by claim 12 wherein said treating comprises a base temperature of about 140° C. and a reflux temperature of about 126° C.

14. The process as defined by claim 13 wherein said treating occurs at substantially atmospheric pressure.

* * * * *